United States Patent
Rubinstenn et al.

(10) Patent No.: US 6,528,043 B2
(45) Date of Patent: *Mar. 4, 2003

(54) COMPOSITION CONTAINING SAPOGENIN

(75) Inventors: Gilles Rubinstenn, Paris (FR); Carole Guiramand, Linas (FR); Francine Baldo, Sceaux (FR); Susanne Dreher, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/945,737

(22) Filed: Sep. 5, 2001

(65) Prior Publication Data

US 2002/0028186 A1 Mar. 7, 2002

Related U.S. Application Data

(63) Continuation of application No. 09/689,595, filed on Oct. 13, 2000, now Pat. No. 6,294,157.

(30) Foreign Application Priority Data

Oct. 14, 1999 (FR) ............................................. 99-12828

(51) Int. Cl.$^7$ ................................................. A61K 7/42
(52) U.S. Cl. ........................ 424/59; 424/401; 424/725; 424/757; 424/765
(58) Field of Search .......................... 424/401, 59, 725, 424/757, 765

(56) References Cited

U.S. PATENT DOCUMENTS

| 4,481,185 A | * 11/1984 | Grollier et al. ................ 424/59 |
| 5,182,373 A | 1/1993 | Kim et al. .................... 536/4.1 |
| 5,279,838 A | 1/1994 | McNeff et al. ................. 426/2 |
| 6,258,386 B1 | 7/2001 | Xia et al. .................... 424/725 |

FOREIGN PATENT DOCUMENTS

| DE | 0 358 970 | 3/1990 |
| DE | 196 31 792 | 3/1997 |
| FR | 2 466 273 | 10/1979 |
| FR | 2 659 556 | 9/1991 |
| GB | 2 080 142 | 2/1982 |

\* cited by examiner

Primary Examiner—Jose' G. Dees
Assistant Examiner—Konata M. George
(74) Attorney, Agent, or Firm—Oblon, Spivak, McClelland, Maier & Neustadt, P.C.

(57) ABSTRACT

A composition comprising, in a physiologically acceptable medium, at least one sapogenin and a solubilizing system comprising: (a) at least one non-emulsifying ester of a fatty acid and/or of a fatty alcohol whose hydrocarbon-based chain contains at least 8 carbon atoms, or a plant oil, and (b) at least one branched fatty alcohol whose hydrocarbon-based chain contains at least 8 carbon atoms and/or at least one lipophilic UV screening agent. The solubilizing system according to the invention makes it possible to dissolve a sufficient amount of sapogenin, without recrystallization, for a period of time which is acceptable for cosmetic or dermatological use.

25 Claims, No Drawings

COMPOSITION CONTAINING SAPOGENIN

BACKGROUND OF THE INVENTION

1. Field of the Invention

The present invention relates to a composition comprising at least one sapogenin in a physiologically acceptable medium.

2. Description of the Background

Sapogenins are compounds resulting from the acid hydrolysis of saponosides, which are heterosides of very high molecular weight present in the plant kingdom. Examples of sapogenins include: diosgenin, hecogenin, smilagenin, sarsapogenin, tigogenin, yamogenin and yuccagenin.

These compounds have in common a steroidal structure comprising a variable number of hydroxyl and/or oxo substituents and/or a variable number of double bonds. They are known as natural chemical precursors of steroidal hormones and are described, in this respect. as constituents of choice for various cosmetic or pharmaceutical preparations. U.S. Pat. No. 5,827,884 also discloses the use of these compounds for their anti-inflammatory properties and as cell growth stimulants.

A preferred sapogenin is diosgenin, or spirost-5-en-3-beta-ol, which can be extracted from fenugreek or from various Dioscorea plants, for example from the root of wild yam.

However, it has been found that diosgenin is difficult to dissolve, and thus to formulate, in solvents that are physiologically acceptable for topical application to the skin, on account of its high melting point (close to 204–207° C.) and its tendency to recrystallize in these solvents.

SUMMARY OF THE INVENTION

It is an object of the present invention to provide a physiologically acceptable means for dissolving diosgenin and the other sapogenins of similar structure, in an amount which is sufficient to obtain the desired effect and for a period of time which is sufficient, at room temperature, to give the composition containing sapogenin a suitable shelf life.

The Inventors have now discovered that the use of a specific solubilizing system allows this object to be achieved.

Accordingly, the objects of the invention, and others, may be accomplished with a composition comprising, in a physiologically acceptable medium, at least one sapogenin and a solubilizing system comprising:

(a) at least one non-emulsifying ester of a fatty acid whose hydrocarbon-based chain contains at least 8 carbon atoms and/or of a fatty alcohol whose hydrocarbon-based chain contains at least 8 carbon atoms, or a plant oil, and (b) at least one branched fatty alcohol whose hydrocarbon-based chain contains at least 8 carbon atoms and/or at least one lipophilic UV screening agent.

The inventors have demonstrated that, although emulsifying esters such as polysorbates do not dissolve sapogenins, certain non-emulsifying esters of fatty alcohols and/or of fatty acids, such as $C_{12-15}$ alkyl benzoate or castor oil, make it possible, by themselves alone, to dissolve an amount of sapogenin ranging up to 3% by weight, relative to the total weight of the sapogenin and solvent. However, the solution obtained recrystallizes after 3 days. It has also been demonstrated that an amount of sapogenin limited to 2% can be dissolved, without recrystallization for at least 7 days, in certain branched fatty alcohols, such as octyldodecanol, and in certain lipophilic UV screening agents, including octyl methoxycinnamate.

However, these first results were difficult to exploit for a commercial use of sapogenins. Moreover, although lipophilic UV screening agents and fatty alcohols are good sapogenin solvents per se, their use in large amount in products for topical application to the skin is not recommended. The reason for this is that the screening agents are relatively expensive. In addition, they have a strong influence on the rheology of the compositions containing them, such that they restrict the freedom of formulation of these compositions in terms of texture. Fatty alcohols, for their part, have a tendency to irritate and dry out the skin.

A more complete appreciation of the invention and many of the attendant advantages thereof will be readily obtained as the same becomes better understood by reference to the following detailed description.

DETAILED DESCRIPTION OF THE INVENTION

The present invention is based on the discovery that certain combinations of two of these solubilizing compounds offer synergism in the solubilization of sapogenin, in the sense that at least one of the following effects is obtained (relative to the compounds taken individually):

the dissolution temperature is lowered, the crystallization is impeded, or even prevented, and the amount of sapogenin dissolved is increased.

This synergistic effect was thus demonstrated for the combination of a plant oil or a non-emulsifying ester of a fatty alcohol and/or of a fatty acid with a branched fatty alcohol and for the combination of this ester with a lipophilic UV screening agent. These combinations also have the advantage of reducing the amount of fatty alcohol or of screening agent required to dissolve diosgenin, by replacing some of these compounds with an ester which offers the formulator full scope as regards the choice of the type of texture which may be envisaged for the composition. The nonemulsifying ester of a fatty alcohol and/or of a fatty acid also has good emollient properties and has the advantage of being relatively cost effective.

It is thus necessary and sufficient that the composition according to the invention should contain at least one of the pairs of compounds mentioned above. However, for cosmetic reasons, it will occasionally be advantageous to make use of a ternary mixture of these three solubilizing agents.

Thus, in one preferred embodiment, the composition according to the invention contains a solubilizing system comprising: (a) at least one nonemulsifying ester of a fatty acid and/or of a fatty alcohol whose hydrocarbon-based chain contains at least 8 carbon atoms, or a plant oil, (b) at least one branched fatty alcohol whose hydrocarbon-based chain contains at least 8 carbon atoms, and (c) at least one lipophilic UV screening agent.

The sapogenin may be chosen from: diosgenin, hecogenin, smilagenin, sarsapogenin, tigogenin, yamogenin and yuccagenin. However, the present invention relates more particularly to diosgenin. This compound can be extracted from Dioscorea tubers by a process comprising, successively: hydrolysis of the heterosides in a mineral acid medium (optionally after fermentation and drying of the tubers); and filtration of the insoluble fraction, which is then neutralized, washed and treated with an apolar solvent. However, other extraction processes can be used. Diosgenin is also commercially available from Sigma under the trade name Diosgenin.

The sapogenin can represent from 0.001% to 10% and preferably from 0.05% to 5% of the total weight of the composition according to the invention. These ranges for the amount of sapogenin in the composition include all specific values and subranges therebetween, such as 0.002, 0.005, 0.01, 0.02, 0.08, 0.1, 0.2, 0.5, 1, 1.5, 2, 3 and 4% of the total weight of the composition.

The constituents of the solubilizing system according to the invention will now be described in greater detail below.

Non-emulsifying Ester of a Fatty Acid and/or of a Fatty Alcohol

The ester forming the first component of the solubilizing system according to the invention can be a mono-, di- or triester obtained from a fatty acid whose hydrocarbon-based chain contains at least 8 carbon atoms and/or from a fatty alcohol whose hydrocarbon-based chain contains at least 8 carbon atoms. This ester has no emulsifying properties, i.e. it generally bears no polar groups such as oxyalkylenated groups or sulphate or phosphate functions, for example, which are liable to give it an amphiphilic nature.

Monoesters which are preferably used are a monoester of a branched fatty alcohol and/or of a branched fatty acid. It is even more advantageous for the fatty acid and the fatty alcohol both to be branched. Examples of such esters are: isononyl isononanoate, isodecyl neopentanoate, octyldodecyl neopentanoate, isostearyl isostearate and isocetyl stearate. As a variant, however, the fatty chain of the alcohol and/or the acid forming the monoester according to the invention can be linear, as in the case of isopropyl myristate.

Diesters which can be used include diesters of a monocarboxylic acid and of a diol, such as propylene glycol dicaprylate and propylene glycol diisostearate.

Triesters which are advantageously used include triesters of a monocarboxylic fatty acid and of glycerol. Examples which may be mentioned are glyceryl triisostearate or caprylic/capric triglycerides.

As a variant, the non-emulsifying ester of a fatty acid and/or of a fatty alcohol according to the invention can be replaced with a plant oil such as apricot kernel oil, castor oil, sunflower oil, groundnut oil, grapeseed oil, walnut oil, etc.

The ester or the plant oil according to the invention can be used in a proportion of from 0.1% to 80% by weight, preferably from 1% to 50% by weight and better still from 5% to 15% by weight, relative to the total weight of the composition. These ranges include all specific values and subranges therebetween, such as 0.2, 0.5, 2, 8, 10, 20, 25, 30, 60, 70 and 75% by weight, relative to the total weight of the composition Branched Fatty Alcohol The branched fatty alcohol constituting one of the compounds which can be used as second component of the solubilizing system according to the invention is such that its hydrocarbon-based chain contains at least 8 carbon atoms. It is preferably a Guerbet alcohol or a 2-alkylalkanol.

Examples of Guerbet alcohols which can be used are: butyloctanol, hexyldecanol, octyldecanol, isostearyl alcohol, octyldodecanol, decyltetradecanol, undecylpentadecanol, dodecylhexadecanol, tetradecyloctadecanol, hexyldecyloctadecanol, tetradecyleicosanol and cetylarachidol. Hexyldecanol is preferably used.

The fatty alcohol according to the invention usually represents from 0.1% to 30%, preferably from 1% to 25% and better still from 1% to 20%, relative to the total weight of the composition. These ranges include all specific values and subranges therebetween, such as 0.2, 0.5, 2, 5, 10, 15 and 18% by weight, relative to the total weight of the composition Lipophilic UV Screening Agent The second component in the solubilizing system according to the invention can consist, instead of, or in addition to, the above fatty alcohol, of a lipophilic UV screening agent.

As lipophilic sunscreens which are suitable for use in the present invention, mention may be made in particular of: p-aminobenzoic acid derivatives, such as p-aminobenzoic acid esters, salts or amides; salicylic acid derivatives such as salicylic acid esters or salts; benzophenone derivatives; dibenzoylmethane derivatives; diphenylacrylate derivatives; benzofuran derivatives; polymeric UV screening agents containing one or more organosilicon residues; cinnamic acid esters; camphor derivatives; trianilino-s-triazine derivatives; phenylbenzimidazolesulphonic acid and its salts; urocanic acid or its ethyl ester; benzotriazoles; hydroxyphenyltriazine derivatives; bis-resorcinol-dialkylaminotriazines; and mixtures thereof.

The lipophilic sunscreen according to the invention is preferably chosen from: octyl salicylate; benzophenone-3; butylmethoxydibenzoylmethane; octocrylene; octyl methoxycinnamate and the compound of formula (II) below, or 2-(2H-benzotriazol-2-yl)-4-methyl-6-[2-methyl-3-[1,3,3,3-tetramethyl-1-[(trimethylsilyl)oxy]disiloxanyl]-propynyl] phenol, described in patent application EP-A-0 392 883 (incorporated herein by reference):

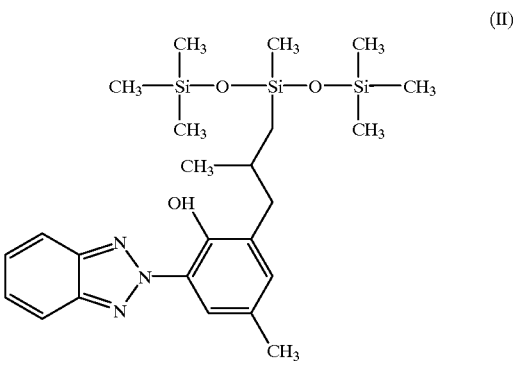

The amount of lipophilic UV screening agent used in the present invention not only depends on the amount of sapogenin to be dissolved and on the amounts of the other co-solvents above, but also is a function of the sun protection factor (SPF) which it is desired to give to the composition. The screening agent can thus represent from 0.001% to 30% of the total weight of the composition. When the composition is intended for daily skin care, an amount of UV screening agent representing from 1% to 10% of the total weight of the composition is preferably used. These ranges include all specific values and subranges therebetween, such as 0.002, 0.005, 0.01, 0.02, 0.05, 0.1, 0.2, 0.5, 2, 5, 12, 20 and 25% of the total weight of the composition.

The composition according to the invention can be in any pharmaceutical form normally used for topical application to the skin, in particular in the form of an oily solution, an oil-in-water or water-in-oil or multiple emulsion, a silicone emulsion, a microemulsion or nanoemulsion, an oily gel, a liquid, pasty or solid anhydrous product, a dispersion of oil in an aqueous phase in the presence of spherules, it being possible for these spherules to be polymer nanoparticles such as nanospheres and nanocapsules or, better still, lipid vesicles of ionic and/or nonionic type.

This composition may be more or less fluid and may have the appearance of a white or colored cream, an ointment, a milk, a lotion, a serum, a paste, a mousse or a gel. It can optionally be applied to the skin in the form of an aerosol. It can also be in solid form and, for example, in the form of a stick. It can be used as a care product and/or as a make-up product for the skin, or as a hair product, for example as a shampoo or conditioner.

In a known manner, the composition of the invention can also contain the adjuvants that are common in cosmetics and dermatology, such as hydrophilic or lipophilic gelling agents, hydrophilic or lipophilic active agents, preserving agents, antioxidants, solvents, fragrances, fillers, pigments, hydrophilic screening agents, odor absorbers and dyestuffs. The amounts of these various adjuvants are those conventionally used in the fields under consideration, and, for example, from 0.01% to 20% relative to the total weight of the composition. Depending on their nature, these adjuvants can be introduced into the fatty phase, into the aqueous phase, into the lipid vesicles and/or into the nanoparticles.

When the composition according to the invention is an emulsion, the proportion of the fatty phase can range from 5% to 80% by weight and preferably from 5% to 50% by weight relative to the total weight of the composition. These ranges include all specific values and subranges therebetween, such as 10, 25, 35, 60 and 70% of the total weight of the composition.

As fatty substances which can be used in the invention, it is possible to use, besides the solubilizing system defined above, mineral oils, oils of animal origin, synthetic oils, silicone oils and fluoro oils. Fatty substances which can also be used include fatty acids, waxes and gums and in particular silicone gums. However, the use of hydrogenated polyisobutene is not recommended, nor are liquid paraffin and petroleum jelly, since these compounds have a tendency to act as counter-solvents with respect to the sapogenin.

The emulsifiers and co-emulsifiers optionally used in the composition in emulsion form are chosen from those used conventionally in the field under consideration. These emulsifiers and co-emulsifiers are preferably present in the composition in a proportion ranging from 0.3% to 30% by weight, and preferably from 0.5% to 20% by weight, relative to the total weight of the composition. As emulsifiers and co-emulsifiers which can be used in the invention, it is particularly advantageous to use esters of a fatty acid and of a polyol, such as PEG-100 stearate, PEG-50 stearate and PEG-40 stearate; sorbitan tristearate, oxyethylenated sorbitan stearates available under the trade names Tweene® 20 or Tween® 60, for example; and mixtures thereof.

Hydrophilic gelling agents which may be mentioned in particular are carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as Bentones, metal salts of fatty acids and hydrophobic silica.

Active agents which can be used in particular include depigmenting agents, emollients, moisturizers, antiseborrhoeic agents, anti-acne agents, agents for promoting regrowth of the hair, keratolytic and/or desquamating agents, anti-wrinkle agents, anti-irritant agents and calmants, and mixtures thereof.

In the event of incompatibility with each other or with the sapogenin, the active agents indicated above and/or the sapogenin can be incorporated into spherules, in particular ionic or nonionic vesicles and/or nanoparticles (nanocapsules and/or nanospheres), so as to isolate them from each other in the composition.

As will be readily appreciated, a person skilled in the art will take care to select the optional compounds to be added to the compositions according to the invention, as well as the concentration thereof, such that the advantageous properties intrinsically associated with the compositions in accordance with the invention are not, or are not substantially, adversely affected by the addition envisaged. In particular, these compounds should not harm the advantageous properties of the sapogenin, or favor its recrystallization.

The present invention also relates to a process for dissolving a sapogenin, characterized in that it comprises the step consisting in mixing the sapogenin with a solubilizing system comprising:

(a) at least one non-emulsifying ester of a fatty acid and/or of a fatty alcohol whose hydrocarbon-based chain contains at least 8 carbon atoms, or a plant oil, and (b) at least one branched fatty alcohol whose hydrocarbon-based chain contains at least 8 carbon atoms, and/or at least one lipophilic UV screening agent.

The mixing of the sapogenin and of the solubilizing system is generally carried out under hot conditions, for example at a temperature in the region of 70° C.

EXAMPLES

Having generally described this invention, a further understanding can be obtained by reference to certain specific examples which are provided herein for purposes of illustration only and are not intended to be limiting unless otherwise specified.

Example 1

Dissolution in a Mixture of a Triester of a Branched Fatty Acid and of a Polyol/Branched Fatty Alcohol Three compositions were prepared, each comprising 2% by weight of diosgenin obtained from Sigma in a different solvent, namely:

For composition 1A: triglyceryl triisostearate available from Stearinerie Dubois under this trade name.

For composition 1B: hexyldecanol available from Condea under the trade name Isofol 16.

For composition 1C: a 50/50 mixture (by weight) of triglyceryl triisostearate and of hexyldecanol.

The above compositions were prepared in the following way. 100 mg of diosgenin were weighed out and placed in a hermetic pillbox, to which 4.9 g of the solvent(s) were added with magnetic stirring at 25° C. for not more than one hour. In the event that the diosgenin was not dissolved after one hour, the suspension was heated with stirring to 50° C. on a waterbath and then, in the absence of dissolution of the diosgenin after one hour at this temperature, the temperature of the suspension was raised to 70° C.

The results obtained are collated in Table 1 below.

TABLE 1

| Composition | Dissolution temperature | Delay in crystallization |
|---|---|---|
| 1A | insoluble | insoluble |
| 1B | 70° C. | 3 days |
| 1C | 50° C. | >15 days* |

*Duration of the experiment

The above procedure was repeated, varying the amount of diosgenin placed in solution. It was thus shown that the maximum amount of diosgenin which can be dissolved at 50° C. in the mixture of solvents was 2%, whereas it was only 1% in each of the solvents taken individually.

It results from the above findings that the mixture of non-emulsifying ester and of branched fatty alcohol potentiates the effects of these compounds with regard to the dissolution of diosgenin.

Example 2

Dissolution in a Mixture of a Monoester of a Linear Fatty Acid and of a Branched Fatty Alcohol/ Branched Fatty Alcohol In the same way as in Example 1, three compositions were prepared, each comprising 2% by weight of diosgenin supplied by Sigma in a different solvent, namely:

For composition 2A: isopropyl myristate available from Stearinerie Dubois under this trade name.

For composition 2B: hexyldecanol available from Condea under the trade name Isofol 16.

For composition 2C: a 50/50 (by weight) mixture of isopropyl myristate and hexyldecanol.

The results obtained are collated in Table 2 below.

TABLE 2

| Composition | Dissolution temperature | Delay in crystallization |
|---|---|---|
| 2A | 70° C. | 2 days |
| 2B | 70° C. | 3 days |
| 2C | 25° C. | >15 days* |

*Duration of the experiment

The above procedure was repeated, varying the amount of diosgenin placed in solution. It was thus shown that the maximum amount of diosgenin which can be dissolved at 50° C. in the mixture of solvents was 4%, whereas it was only 1% in each of the solvents taken individually.

It results from the above findings that the mixture of non-emulsifying ester and of branched fatty alcohol potentiates the effects of these compounds with regard to the dissolution of diosgenin.

Example 3

Dissolution in a Mixture of a Monoester of a Branched Fatty Alcohol and a Branched Fatty Acid/ Branched Fatty Alcohol In the same way as in Example 1, three compositions were prepared, each comprising 2% by weight of diosgenin supplied by Sigma in a different solvent, namely:

For composition 3A: isononyl isononanoate available from Stearinerie Dubois under this trade name.

For composition 3B: hexyldecanol available from Condea under the trade name Isofol 16.

For composition 3C: a 50/50 (by weight) mixture of isononyl isononanoate and hexyldecanol.

The results obtained are collated in Table 3 below.

TABLE 3

| Composition | Dissolution temperature | Delay in crystallization |
|---|---|---|
| 3A | 70° C. | 5 hours |
| 3B | 70° C. | 3 days |
| 3C | 40° C. | >15 days* |

*Duration of the experiment

The above procedure was repeated, varying the amount of diosgenin placed in solution. It was thus shown that the maximum amount of diosgenin which can be dissolved at 50° C. in the mixture of solvents was 3%, whereas it was only 1% in each of the solvents taken individually.

It results from the above findings that the mixture of non-emulsifying ester and of branched fatty alcohol potentiates the effects of these compounds with regard to the dissolution of diosgenin.

Example 4

Dissolution in a Mixture of a Monoester of a Branched Fatty Acid and of a Branched Fatty Alcohol/Lipophilic UV Screening Agent In the same way as in Example 1, three compositions were prepared, each comprising 2% by weight of diosgenin supplied by Sigma in a different solvent, namely:

For composition 4A: isononyl isononanoate available from Stearinerie Dubois under this trade name.

For composition 4B: octyl methoxycinnamate available from Givaudan under the trade name Parsol MCX.

For composition 4C: a 50/50 (by weight) mixture of isononyl isononanoate and octyl methoxycinnamate.

The results obtained are collated in Table 4 below.

TABLE 4

| Composition | Dissolution temperature | Delay in crystallization |
|---|---|---|
| 4A | 70° C. | 5 hours |
| 4B | 50° C. | 7 days |
| 4C | 50° C. | 7 days |

The amount of diosgenin placed in solution was then varied. It was thus shown that the maximum amount of diosgenin which can be dissolved at 50° C. in the mixture of solvents was 3%, whereas it was only 1% in the ester and 2% in the UV screening agent.

It results from the above findings that the mixture of ester and of screening agent potentiates the effects of these compounds with regard to the amount of diosgenin which can be dissolved in these solvents. In addition, the dissolution of 2% of diosgenin takes place both in the mixture of solvents and in the screening agent alone, thereby making it possible to use this screening agent at lower doses and thus to improve the cosmetic qualities of the composition and its manufacturing cost.

Example 5

Cosmetic Composition

The composition below was prepared:

| Phase A1 | |
|---|---|
| Demineralized water | 58.30% |
| Preserving agent | 0.25% |
| Carbomer | 0.40% |
| Glycerol | 3.00% |
| Xanthan gum | 0.10% |
| Phase A2 | |
| 20 EO oxyethylenated sorbitan stearate (Polysorbate 60) | 0.90% |
| Phase B | |
| PEG-100 stearate and glyceryl stearate | 2.10% |
| Cetyl alcohol | 2.60% |
| Isononyl isononanoate | 11.50% |
| Octyldodecanol | 15.00% |
| Diosgenin | 0.50% |
| Butyl hydroxytoluene | 0.10% |
| Octyl methoxycinnamate | 1.00% |
| Preserving agents | 0.15% |
| Phase C | |
| Demineralized water | 2.00% |
| Triethanolamine | 0.30% |
| Phase D | |
| Demineralized water | 1.50% |
| Preserving agent | 0.30% |

The constituents of phase A1 are mixed together at 70° C., with stirring. The constituents of phase A2 and B are mixed together and heated at 70° C. on a waterbath, and the mixture is then emulsified in phase A1 at the same temperature, with stirring at 600 rpm for about two minutes. Phase C is prepared at room temperature, by dissolving the triethanolamine in the water, with magnetic stirring, and is then added at about 800 rpm to the above mixture, which is then left to cool. Phase D is prepared in the same manner as phase C and added to the mixture cooled to below 50° C. The composition is then left to cool to room temperature.

An examination by microscope of the composition obtained shows that the emulsion is fine, uniform, has sharp boundaries and contains no crystals. In addition, physico-chemical analysis of the composition shows that it is stable after storage for two months at 4° C., 25° C. and 45° C. In particular, no recrystallization of the diosgenin is observed after this period of time, at the temperatures indicated. In addition, the chemical stability of the diosgenin, as determined by HPLC, is not affected.

Example 6

Cosmetic Composition

The composition below was prepared in the same way as in Example 5:

| Phase A1 | |
|---|---|
| Demineralized water | 57.80 |
| Preserving agent | 0.25% |
| Carbomer | 0.40% |
| Glycerol | 3.00% |
| Xanthan gum | 0.10% |
| Phase A2 | |
| 20 EO oxyethylenated sorbitan stearate (Polysorbate 60) | 0.90% |
| Phase B | |
| PEG-100 stearate and glyceryl stearate | 2.10% |
| Cetyl alcohol | 2.60% |
| Isononyl isononanoate | 11.00% |
| Octyldodecanol | 15.00% |
| Diosgenin | 0.50% |
| Butyl hydroxytoluene | 0.10% |
| Octocrylene | 2.00% |
| Preserving agents | 0.15% |
| Phase C | |
| Demineralized water | 2.00% |
| Triethanolamine | 0.30% |
| Phase D | |
| Demineralized water | 1.50% |
| Preserving agent | 0.30% |

An examination by microscope of the composition obtained shows that the emulsion is fine, uniform, has sharp boundaries and contains no crystals. In addition, physico-chemical analysis of the composition shows that it is stable after storage for two months at 4° C., 25° C. and 45° C. In particular, no recrystallization of the diosgenin is observed after this period of time, at the temperatures indicated. In addition, the chemical stability of the diosgenin, as determined by HPLC, is not affected.

Example 7

Cosmetic Composition

The composition below was prepared in the same way as in Example 5:

| Phase A1 | |
|---|---|
| Demineralized water | 66.70% |
| Preserving agent | 0.25% |
| Carbomer | 0.40% |
| Glycerol | 3.00% |
| Xanthan gum | 0.10% |
| Phase A2 | |
| 20 EO oxyethylenated sorbitan stearate (Polysorbate 60) | 0.90% |
| Phase B | |
| PEG-100 stearate and glyceryl stearate | 2.10% |
| Cetyl alcohol | 2.60% |
| Isononyl isononanoate | 6.00% |
| Octyldodecanol | 7.50% |
| Diosgenin | 0.10% |
| Butyl hydroxytoluene | 0.10% |
| Caprylic/capric triglycerides | 6.00% |
| Preserving agents | 0.15% |
| Phase C | |
| Demineralized water | 2.00% |
| Triethanolamine | 0.30% |
| Phase D | |
| Demineralized water | 1.50% |
| Preserving agent | 0.30% |

An examination by microscope of the composition obtained shows that the emulsion is fine, uniform, has sharp boundaries and contains no crystals. In addition, physicochemical analysis of the composition shows that it is stable after storage for two months at 4° C., 25° C. and 45° C. In particular, no recrystallization of the diosgenin is observed after this period of time, at the temperatures indicated. In addition, the chemical stability of the diosgenin, as determined by HPLC, is not affected.

Example 8

Cosmetic Composition

The composition below was prepared in the same way as in Example 5:

| Phase A1 | |
|---|---|
| Demineralized water | 66.70% |
| Preserving agent | 0.25% |
| Carbomer | 0.40% |
| Glycerol | 3.00% |
| Xanthan gum | 0.10% |
| Phase A2 | |
| 20 EO oxyethylenated sorbitan stearate (Polysorbate 60) | 0.90% |
| Phase B | |
| PEG-100 stearate and glyceryl stearate | 2.10% |
| Cetyl alcohol | 2.60% |
| Isononyl isononanoate | 6.00% |
| Octyldodecanol | 7.50% |
| Diosgenin | 0.10% |
| Butyl hydroxytoluene | 0.10% |
| Apricot kernel oil | 6.00% |
| Preserving agents | 0.15% |
| Phase C | |
| Demineralized water | 2.00% |
| Triethanolamine | 0.30% |
| Phase D | |
| Demineralized water | 1.50% |
| Preserving agent | 0.30% |

An examination by microscope of the composition obtained shows that the emulsion is fine, uniform, has sharp boundaries and contains no crystals. In addition, physicochemical analysis of the composition shows that it is stable after storage for two months at 4° C., 25° C. and 45° C. In particular, no recrystallization of the diosgenin is observed after this period of time, at the temperatures indicated. In addition, the chemical stability of the diosgenin, as determined by HPLC, is not affected.

Example 9

Cosmetic Composition

The composition below was prepared in the same way as in Example 5:

| Phase A1 | |
|---|---|
| Demineralized water | 60.80 |
| Preserving agent | 0.25% |
| Carbomer | 0.40% |
| Glycerol | 3.00% |
| Xanthan gum | 0.10% |
| Phase A2 | |
| 20 EO oxyethylenated sorbitan stearate (Polysorbate 60) | 0.90% |
| Phase B | |
| PEG-100 stearate and glyceryl stearate | 2.10% |
| Cetyl alcohol | 2.60% |
| Isononyl isononanoate | 9.00% |
| Octyldodecanol | 10.00% |
| Diosgenin | 0.50% |
| Butyl hydroxytoluene | 0.10% |
| Octyl methoxycinnamate | 6.00% |
| Preserving agents | 0.15% |
| Phase C | |
| Demineralized water | 2.00% |
| Triethanolamine | 0.30% |
| Phase D | |
| Demineralized water | 1.50% |
| Preserving agent | 0.30% |

An examination by microscope of the composition obtained shows that the emulsion is fine, uniform, has sharp boundaries and contains no crystals. In addition, physicochemical analysis of the composition shows that it is stable after storage for two months at 4° C., 25° C. and 45° C. In particular, no recrystallization of the diosgenin is observed after this period of time, at the temperatures indicated. In addition, the chemical stability of the diosgenin, as determined by HPLC, is not affected.

Example 10

Cosmetic Composition

The composition below was prepared in the same way as in Example 5:

| Phase A1 | |
|---|---|
| Demineralized water | 58.80% |
| Preserving agent | 0.25% |
| Carbomer | 0.40% |
| Glycerol | 3.00% |
| Xanthan gum | 0.10% |
| Phase A2 | |
| 20 EO oxyethylenated sorbitan stearate (Polysorbate 60) | 0.90% |
| Phase B | |
| PEG-100 stearate and glyceryl stearate | 2.10% |
| Cetyl alcohol | 2.60% |
| Isononyl isononanoate | 7.00% |
| octyldodecanol | 10.00% |
| Diosgenin | 0.50% |
| Butyl hydroxytoluene | 0.10% |
| Octocrylene | 10.00% |
| Preserving agents | 0.15% |
| Phase C | |
| Demineralized water | 2.00% |
| Triethanolamine | 0.30% |
| Phase D | |
| Demineralized water | 1.50% |
| Preserving agent | 0.30% |

An examination by microscope of the composition obtained shows that the emulsion is fine, uniform, has sharp boundaries and contains no crystals. In addition, physicochemical analysis of the composition shows that it is stable after storage for two months at 4° C., 25° C. and 45° C. In particular, no recrystallization of the diosgenin is observed after this period of time, at the temperatures indicated. In addition, the chemical stability of the diosgenin, as determined by HPLC, is not affected.

Example 11

Cosmetic Composition

The composition below was prepared in the same way as in Example 5:

| | |
|---|---|
| Phase A1 | |
| Demineralized water | 63.30% |
| Preserving agent | 0.25% |
| Carbomer | 0.40% |
| Glycerol | 3.00% |
| Xanthan gum | 0.10% |
| Phase A2 | |
| 20 EO oxyethylenated sorbitan stearate (Polysorbate 60) | 0.90% |
| Phase B | |
| PEG-100 stearate and glyceryl stearate | 2.10% |
| Cetyl alcohol | 2.60% |
| Isononyl isononanoate | 11.50% |
| octyldodecanol | 10.00% |
| Diosgenin | 0.50% |
| Butyl hydroxytoluene | 0.10% |
| Octyl methocycinnamate | 1.00% |
| Preserving agents | 0.15% |
| Phase C | |
| Demineralized water | 2.00% |
| Triethanolamine | 0.30% |
| Phase D | |
| Demineralized water | 1.50% |
| Preserving agent | 0.30% |

An examination by microscope of the composition obtained shows that the emulsion is fine, uniform, has sharp boundaries and contains no crystals. In addition, physicochemical analysis of the composition shows that it is stable after storage for two months at 4° C., 25° C. and 45° C. In particular, no recrystallization of the diosgenin is observed after this period of time, at the temperatures indicated. In addition, the chemical stability of the diosgenin, as determined by HPLC, is not affected.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-12828, filed on Oct. 14, 1999, the entire of contents of which is incorporated herein by reference.

What is claimed is:

1. A composition comprising, in a physiologically acceptable medium, at least one sapogenin, and a solubilizing system comprising:
   (a) at least one non-emulsifying ester of a fatty acid and/or of a fatty alcohol having a hydrocarbon-based chain containing at least 8 carbon atoms, or a plant oil, and
   (b) at least one lipophilic UV screening agent.

2. The composition of claim 1, wherein the solubilizing system comprises an ester which is a monoester of a branched fatty alcohol and/or of a branched fatty acid.

3. The composition of claim 2, wherein the solubilizing system comprises an ester which is selected from the group consisting of isononyl isononanoate, isodecyl neopentanoate, octyldodecyl neopentanoate, isostearyl isostearate and isocetyl stearate.

4. The composition of claim 1, wherein the solubilizing system comprises an ester which is a diester of a monocarboxylic acid and/or of a diol.

5. The composition of claim 4, wherein the solubilizing system comprises an ester which is selected from the group consisting of propylene glycol dicaprylate and propylene glycol diisostearate.

6. The composition of claim 1, wherein the solubilizing system comprises an ester which is a triester of a monocarboxylic fatty acid and/or of glycerol.

7. The composition of claim 6, wherein the solubilizing system comprises an ester which is selected from the group consisting of glyceryl triisostearate or caprylic/capric triglycerides.

8. The composition of claim 1, wherein the ester represents from 1% to 50% relative to the total weight of the composition.

9. The composition of claim 1, wherein the ester represents from 5% to 15% relative to the total weight of the composition.

10. The composition of claim 1, wherein the lipophilic UV screening agent is selected from the group consisting of p-aminobenzoic acid derivatives, salicylic acid derivatives, benzophenone derivatives, dibenzoylmethane derivatives, diphenylacrylate derivatives, benzofuran derivatives, polymeric UV screening agents containing one or more organosilicon residues, cinnamic acid esters, camphor derivatives, trianilino-s-triazine derivatives, phenylbenzimidazolesulphonic acid and salts thereof, urocanic acid or its ethyl ester, benzotriazoles, hydroxyphenyltriazine derivatives, bis-resorcinol-dialkylaminotriazines, and mixtures thereof.

11. The composition of claim 1, wherein the lipophilic UV screening agent is a salicylic acid derivative.

12. The composition of claim 1, wherein the lipophilic UV screening agent is octyl salicylate.

13. The composition of claim 1, wherein the lipophilic UV screening agent is a benzophenone derivative.

14. The composition of claim 1, wherein the lipophilic UV screening agent is benzophenone-3.

15. The composition of claim 1, wherein the lipophilic UV screening agent is butylmethoxydibenzoylmethane.

16. The composition of claim 1, wherein the lipophilic UV screening agent is octylcrylene.

17. The composition of claim 1, wherein the lipophilic UV screening agent is octyl methoxycinnamate.

18. The composition of claim 1, wherein the lipophilic UV screening agent is 2-(2H-benzotriazol- 2-yl)-4-methyl-6-[2-methyl-3-[1,3,3,3-tetramethyl- 1-[(trimethylsilyl)oxy]disiloxanyl]-propynol]phenol.

19. The composition of claim 1, wherein the screening agent represents from 1% to 10% relative to the total weight of the composition.

20. The composition of claim 1, wherein the sapogenin is selected from the group consisting of diosgenin, hecogenin, smilagenin, sarsapogenin, tigogenin, yamogenin and yuccagenin.

21. The composition of claim 1, wherein the sapogenin is diosgenin.

22. The composition of claim 1, wherein the sapogenin represents from 0.05% to 5% relative to the total weight of the composition.

23. A process for dissolving a sapogenin, comprising mixing the sapogenin with a solubilizing system comprising:

(a) at least one non-emulsifying ester of a fatty acid and/or of a fatty alcohol whose hydrocarbon-based chain contains at least 8 carbon atoms, or a plant oil, and (b) at least one lipophilic UV screening agent.

24. The composition of claim 1, wherein the solubilizing system comprises at least one non-emulsifying ester of a fatty acid and/or of a fatty alcohol having a hydrocarbon-based chain containing at least 8 carbon atoms.

25. The composition of claim 1, wherein the solubilizing system comprises a plant oil.

* * * * *

UNITED STATES PATENT AND TRADEMARK OFFICE
CERTIFICATE OF CORRECTION

PATENT NO. : 6,528,043 B2
DATED : March 4, 2003
INVENTOR(S) : Gilles Rubinstenn et al.

It is certified that error appears in the above-identified patent and that said Letters Patent is hereby corrected as shown below:

<u>Column 14,</u>
Line 17, "or caprylic/capric triglycerides" should read -- and caprylic/capric triglycerides --.
Line 53, "wherein the screening" should read -- wherein the lipophilic UV screening --.

Signed and Sealed this

Ninth Day of November, 2004

JON W. DUDAS
*Director of the United States Patent and Trademark Office*